(12) United States Patent
Giusti et al.

(10) Patent No.: US 12,156,541 B2
(45) Date of Patent: Dec. 3, 2024

(54) MICROFLUIDIC DISPENSING DEVICE HAVING A PLURALITY OF EJECTION CHAMBERS

(71) Applicant: STMicroelectronics S.r.l., Agrate Brianza (IT)

(72) Inventors: Domenico Giusti, Caponago (IT); Irene Martini, Bergamo (IT)

(73) Assignee: STMicroelectronics S.r.l., Agrate Brianza (IT)

(*) Notice: Subject to any disclaimer, the term of this patent is extended or adjusted under 35 U.S.C. 154(b) by 933 days.

(21) Appl. No.: 17/118,452

(22) Filed: Dec. 10, 2020

(65) Prior Publication Data

US 2021/0177061 A1  Jun. 17, 2021

(30) Foreign Application Priority Data

Dec. 16, 2019  (IT) .................. 102019000024081

(51) Int. Cl.
| | | |
|---|---|---|
| A24F 40/48 | (2020.01) | |
| A24F 40/10 | (2020.01) | |
| A24F 40/30 | (2020.01) | |
| A24F 40/46 | (2020.01) | |
| A24F 40/53 | (2020.01) | |
| A24F 40/70 | (2020.01) | |
| B01L 9/00 | (2006.01) | |
| H05B 1/02 | (2006.01) | |

(52) U.S. Cl.
CPC .............. *A24F 40/48* (2020.01); *A24F 40/10* (2020.01); *A24F 40/30* (2020.01); *A24F 40/46* (2020.01); *A24F 40/53* (2020.01); *A24F 40/70* (2020.01); *B01L 9/527* (2013.01); *H05B 1/0297* (2013.01)

(58) Field of Classification Search
CPC .......... A24F 40/48; A24F 40/10; A24F 40/30; A24F 40/46; A24F 40/53; A24F 40/70; A24F 40/51; A24F 40/44; A24F 40/40; A24F 40/50; B01L 9/527; H05B 1/0297; H05B 1/0227; H05B 3/26; B05B 17/0638; B05B 1/24; B05B 12/04; A61M 11/005; A61M 15/0085; A61M 2202/0468; A61M 2205/3368; A61M 2205/8206; A61M 15/025; A61M 15/06; A61M 11/042; A61M 11/00; A61M 15/0003; A61M 15/0086
See application file for complete search history.

(56) References Cited

U.S. PATENT DOCUMENTS

| | | |
|---|---|---|
| 2018/0141074 A1 | 5/2018 | Giusti et al. |
| 2018/0236445 A1 | 8/2018 | Giusti et al. |
| 2019/0350260 A1 | 11/2019 | Di Marco et al. |

FOREIGN PATENT DOCUMENTS

EP  3 569 275 A1  11/2019

OTHER PUBLICATIONS

Mao et al, High precision digital droplet pipetting enabled by a plug-and—play microfluidic pipetting chip, Lab Chip, 2018, 18, 2720-2729 (Year: 2018).*

* cited by examiner

*Primary Examiner* — Narayan K Bhat
(74) *Attorney, Agent, or Firm* — Seed IP Law Group LLP

(57) ABSTRACT

A microfluidic dispensing device has a plurality of chambers arranged in sequence, each having an inlet receiving a liquid to be dispensed and a nozzle for emitting a drop of liquid. An actuator in each chamber receives an actuation quantity and causes a drop of liquid to be emitted by the nozzle of the respective chamber. A drop emission detection element in each chamber generates an actuation command upon detecting the emission of a drop of liquid. A sequential activation electric circuit includes a plurality of sequential activation elements, one for each chamber, each coupled to the drop emission detection element of the respective chamber and to an actuator associated with a subsequent chamber in the sequence of chambers. Each sequential activation element receives the actuation command from the drop emission detection element associated with the respective chamber and activates the actuator associated with the subsequent chamber in the sequence of chambers.

20 Claims, 8 Drawing Sheets

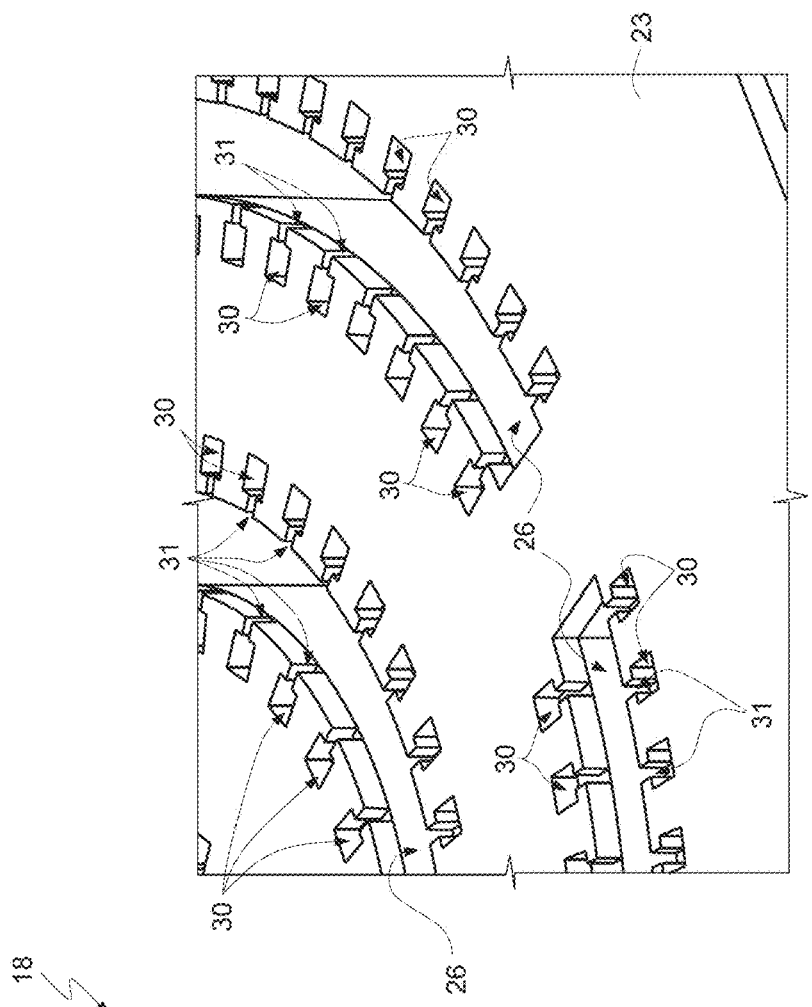
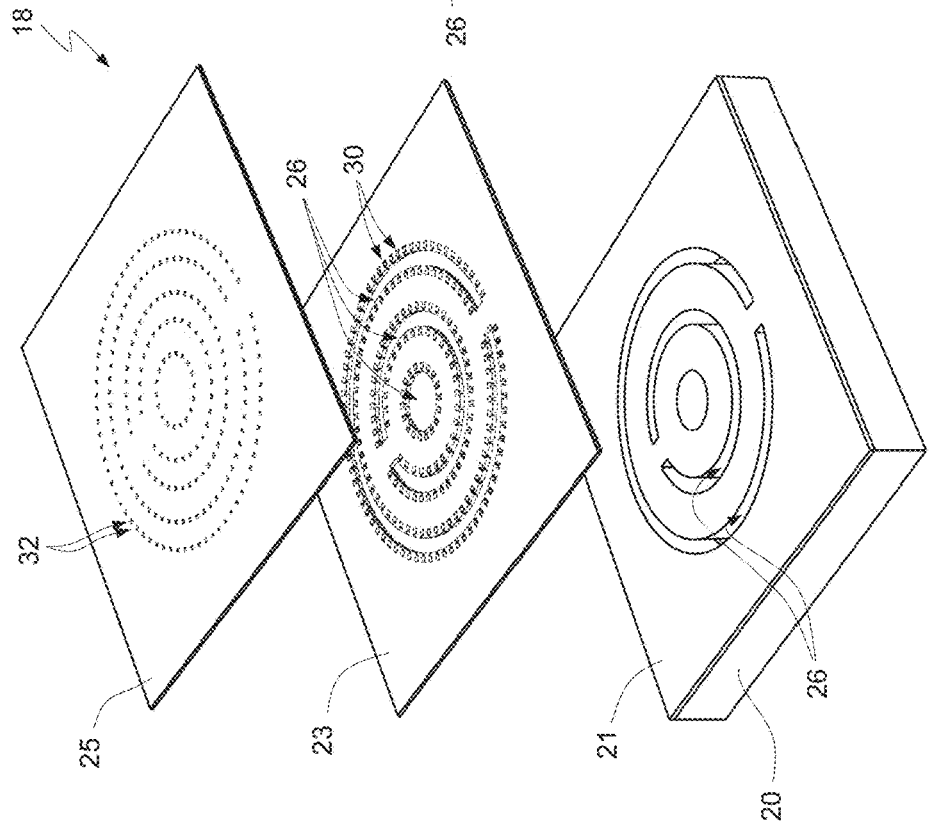
FIG. 2A (Prior Art)
FIG. 2B (Prior Art)

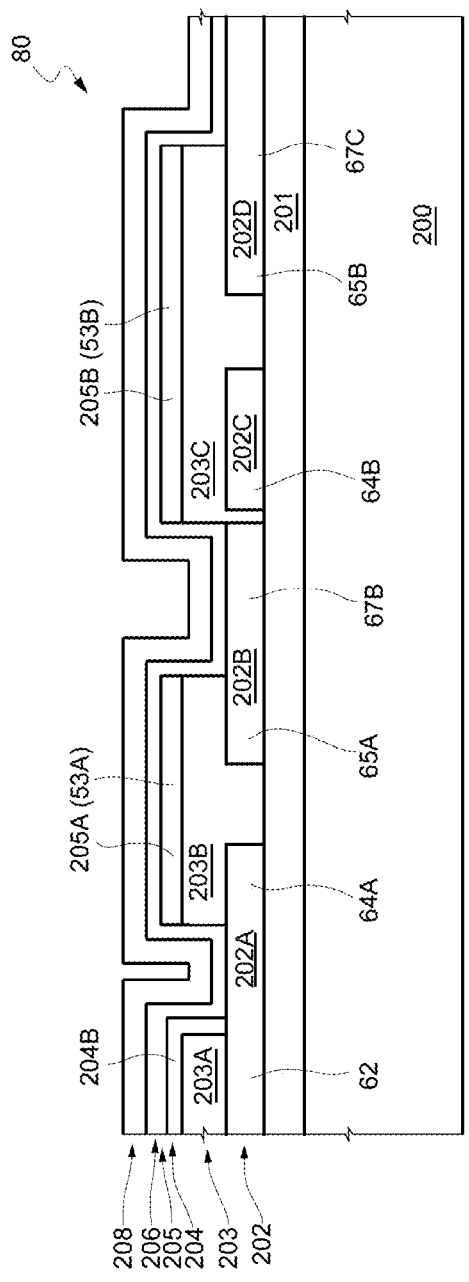
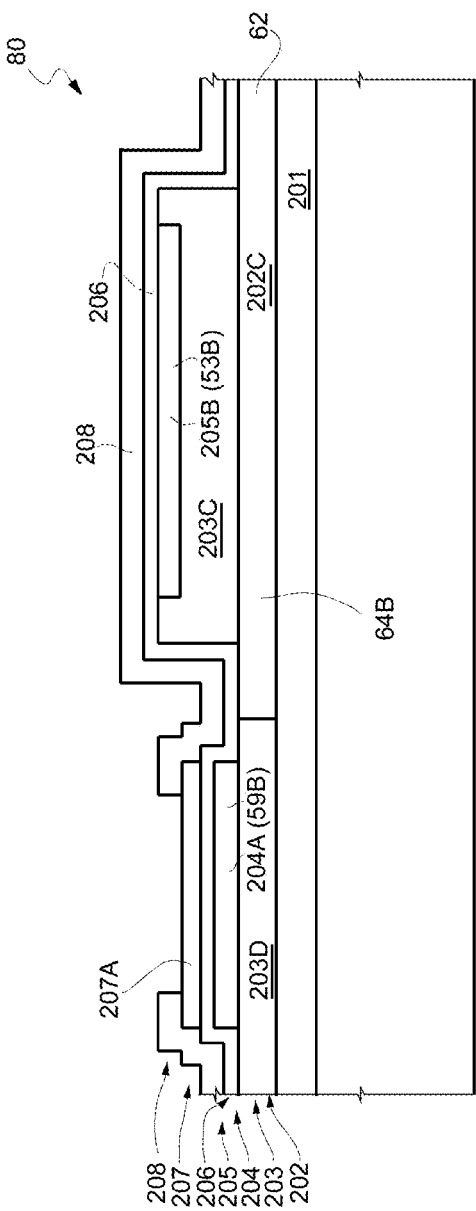
FIG. 7A
FIG. 7B

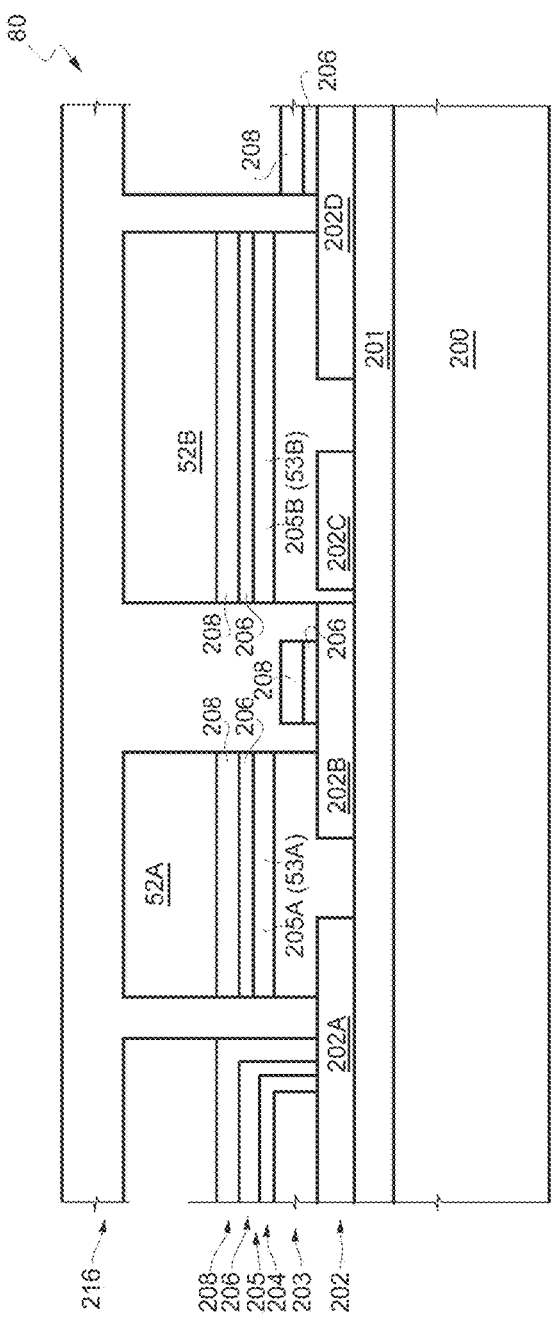
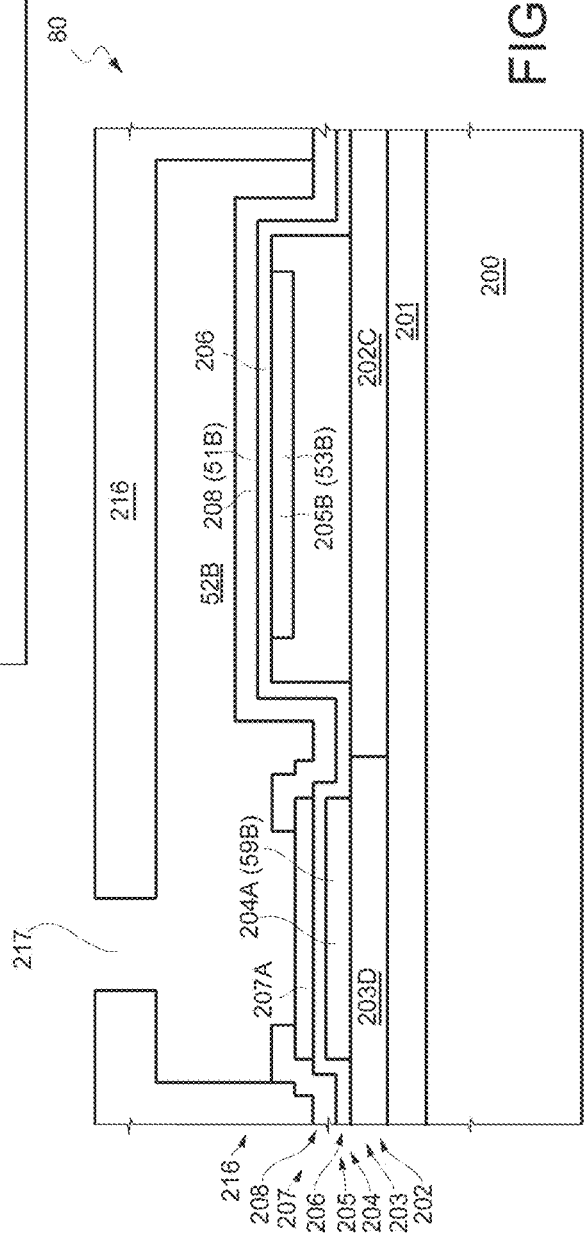
FIG. 10A
FIG. 10B

MICROFLUIDIC DISPENSING DEVICE HAVING A PLURALITY OF EJECTION CHAMBERS

BACKGROUND

Technical Field

The present disclosure relates to a microfluidic dispensing device, in particular of inhalable substances, with a plurality of ejection chambers.

Description of the Related Art

As is known, the desire to accurately control the dispensing of inhalable substances, both for therapeutic purposes and for manufacturing non-medical devices, such as the so-called electronic cigarettes, has led to the development of miniaturized dispensing apparatus that are easily usable.

A miniaturized dispensing apparatus for inhalable substances of known type normally comprises a tank, which contains a fluid with the substances to be dispensed in solution, and at least a dispensing chamber, having ejector nozzles and supplied by the tank. An actuator, accommodated in the chamber and driven by a controller, causes a controlled quantity of fluid to be ejected.

For example, a miniaturized dispensing apparatus of this type is shown in Italian patent application No. 102018000005372 (corresponding to US patent application US 2019/0350260 A1) and briefly described herein below.

In detail, FIG. 1 shows a miniaturized dispensing apparatus 1, here an electronic cigarette. The miniaturized dispensing apparatus 1 comprises a casing 2 accommodating a driver 3, a battery 4 and a microfluidic cartridge 5 of disposable type.

More in detail, the casing 2 forms a control chamber 7 and a cartridge chamber 8. In one embodiment, the control chamber 7 is substantially axial, is open at a first end 2A of the casing 2 and is closable for example with an aesthetic lid, not shown. The driver 3, comprising for example an ASIC (Application Specific Integrated Circuit) 6, may be soldered on a substrate 10, for example a PCB (Printed Circuit Board) insertable into the control chamber 7 together with the battery 4.

The cartridge chamber 8 is arranged between the control chamber 7 and a second end 2B of the casing 2 and is accessible through a flip door 11 for inserting and removing the microfluidic cartridges 5. The cartridge chamber 8 communicates with the outside through inlet holes 13 and a mouthpiece 14. More precisely, the inlet holes 13 and the mouthpiece 14 are arranged so that suction through the mouthpiece 14 causes the air in the cartridge chamber 8 to return through the inlet holes 13, the sucked air to pass through the cartridge chamber 8 and the air to subsequently come out through the mouthpiece 14.

Electrical connection lines 15, for example embedded in the casing 2, extend between the control chamber 7 and the cartridge chamber 8 to electrically couple the driver 3 and the microfluidic cartridge 5 in the cartridge chamber 8.

The microfluidic cartridge 5 comprises a tank 17, containing a liquid to be dispensed, and a spray nozzle 18 controlled by the driver 3 and arranged here on an external face of the microfluidic cartridge 5.

In the embodiment shown in FIGS. 2A and 2B, the spray nozzle 18 comprises a substrate 20 covered by an insulating layer 21, a chamber layer 23 extending above the insulating layer 21, and a nozzle plate 25 bonded to the chamber layer 23. The substrate 20, the insulating layer 21 and the chamber layer 23 may be, for example, respectively, of semiconductor material, silicon oxide or nitride and a polymeric material such as dry film. The nozzle plate 25 may be of polymeric material or semiconductor material.

Supply passages 26 fluidly coupled to the tank 17 (FIG. 1) are formed through the substrate 20, the insulating layer 21 and the chamber layer 23. In the embodiment illustrated in FIGS. 2A and 2B, in particular, the supply passages 26 are circular and concentric.

Chambers 30 are formed in the chamber layer 23 along the supply passages 26, as also shown in FIG. 2B. In the illustrated embodiment, the chambers 30 are distributed uniformly. Furthermore, the chambers 30 are fluidly coupled to the supply passages 26 through respective microfluidic channels 31 and are delimited on the bottom by the insulating layer 21 and on the top by the nozzle plate 25.

Nozzles 32 are formed in the nozzle plate 25 at each chamber 30 and allow, in use, the liquid nebulized by the chambers 30 to pass and to be mixed with the air flowing from the inlet holes 13 through the cartridge chamber 8 towards the mouthpiece 14.

FIG. 3 shows a possible embodiment of a chamber 30. Here, the chamber 30 has a parallelepiped shape and is laterally delimited by walls 30A formed in the chamber layer 23.

A heater 33 is formed here within the insulating layer 21 below the chamber 30. The heater 33 may be formed, in a non-limiting manner, of polycrystalline silicon, Al, Pt, TiN, TiAlN, TaSiN, TiW. The heater 33 is connected to the driver 3 (FIG. 1) through the electrical connection lines 15.

In use, the ASIC 6 (FIG. 1) generates electrical signals supplied to the heaters 33 of the chambers 30 through the connection lines 15, allowing the heaters 33 to heat up to a programmed temperature, for example 450° C. The liquid present in the chambers 30, coming from the tank 17 (FIG. 1) through the supply passages 26 (FIG. 2A), is then rapidly heated and forms vapor bubbles such as to push a drop of liquid through each nozzle 32. As a whole the chambers 30 thus allow vapor "plumes" to be obtained in the cartridge chamber 8.

BRIEF SUMMARY

In prior approaches and applications of dispensing devices, to generate sufficient vapor "plumes" for the specific application, a large number of chambers 30 is generally relied on or utilized, for example greater than one thousand. For example, referring to FIG. 3, the direct driving of each heater 33 through respective connection lines 15 is thus complex, expensive and generally utilized a large integration area for the arrangement of the contact pads and the difficulty of forming the wire connections.

To overcome this problem, it is possible to use a suitable driver, such as the ASIC 6 of FIG. 1, and arrange it within the silicon die wherein the microfluidic cartridge 5 is formed. However, this solution is also expensive and cannot be used in all low-cost applications.

In various embodiments, the present disclosure provides a dispensing device which overcomes the drawbacks of the prior art.

According to the present disclosure, a microfluidic dispensing device, the manufacturing process thereof and a dispensing method are provided.

In at least one embodiment, a microfluidic dispensing device is provided that includes a plurality of chambers, each chamber having an inlet configured to receive a liquid to be dispensed and a nozzle configured to emit a drop of liquid, the plurality of chambers forming a sequence of chambers. A plurality of actuators are included, with each actuator being associated with a respective chamber and configured to receive a respective actuation quantity and cause a drop of liquid to be emitted by the nozzle of the respective chamber. A plurality of drop emission detection elements are included, one for each chamber, each drop emission detection element being configured to generate an actuation command upon detecting the emission of a drop of liquid from the nozzle of a respective chamber. The device further includes a sequential activation electric circuit including a plurality of sequential activation elements, one for each chamber, each sequential activation element being coupled to the drop emission detection element associated with the respective chamber and to an actuator associated with a chamber following the respective chamber in the sequence of chambers, each sequential activation element being configured to receive the actuation command from the drop emission detection element associated with the respective chamber and activate the actuator associated with the subsequent chamber in the sequence of chambers.

In at least one embodiment, a process for manufacturing a microfluidic dispensing device is provided that includes: forming a plurality of chambers, each chamber having an inlet configured to receive a liquid to be dispensed and a nozzle configured to emit a drop of liquid, the plurality of chambers forming a sequence of chambers; forming a plurality of actuators, each actuator being associated with a respective chamber and configured to receive a respective actuation quantity and cause a drop of liquid to be emitted by the nozzle of the respective chamber; forming a plurality of drop emission detection elements, one for each chamber, each drop emission detection element being configured to generate an actuation command upon detecting the emission of a drop of liquid from the nozzle of a respective chamber; and forming a sequential activation electric circuit, including: a plurality of sequential activation elements, one for each chamber, each sequential activation element being coupled to the drop emission detection element associated with the respective chamber and an actuator associated with a chamber following the respective chamber in the sequence of chambers, each sequential activation element being configured to receive the actuation command from the drop emission detection element associated with the respective chamber and activate the actuator associated with the subsequent chamber in the sequence of chambers.

In at least one embodiment, a method for dispensing in a microfluidic dispensing device is provided. The microfluidic dispensing device includes: a plurality of chambers, each chamber having an inlet and a nozzle, the plurality of chambers forming a sequence of chambers; a plurality of actuators, one for each chamber; a plurality of drop emission detection elements, one for each chamber; and a sequential activation electric circuit including: a plurality of sequential activation elements, each sequential activation element being coupled to the drop emission detection element associated with the respective chamber and an actuator associated with a chamber following the respective chamber in the sequence of chambers. The method includes: providing a liquid to be dispensed to the plurality of chambers; activating an actuator of a first chamber of the succession of chambers and causing a drop of liquid to be emitted by the nozzle of the first chamber; detecting the emission of the drop from the first chamber through the sequential activation element associated with the first chamber; and upon detecting the emission of the drop from the first chamber, activating an actuator associated with a chamber following the first chamber through the sequential activation element associated with the first chamber.

BRIEF DESCRIPTION OF THE SEVERAL VIEWS OF THE DRAWINGS

For a better understanding of the present disclosure, embodiments thereof are now described, purely by way of non-limiting example, with reference to the attached drawings, wherein:

FIG. 2A is an exploded perspective view of a microfluidic dispensing device usable in the electronic cigarette of FIG. 1;

FIG. 2B is an enlarged perspective view of a portion of the microfluidic dispensing device of FIG. 2A, with parts removed for clarity;

FIGS. 7A-10A show cross-sections of the present microfluidic dispensing device, taken along section line VIIA-VIIA of FIG. 4A, in subsequent manufacturing steps; and FIGS. 7B-10B show cross-sections of the present microfluidic dispensing device, taken along section line VIIB-VIIB of FIG. 4A, in subsequent manufacturing steps.

DETAILED DESCRIPTION

A microfluidic dispensing device 50 usable in a dispensing apparatus, such as an electronic cigarette, an inhaler for medical use, a CPAP (Continuous Positive Airway Pressure) device, for detecting sleep apneas or in different types of apparatus, such as anti-pollution masks and apparatus for detecting leaks of air or other fluids, used in the industrial or automotive field, is described herein below.

Figures 4A, 4B:
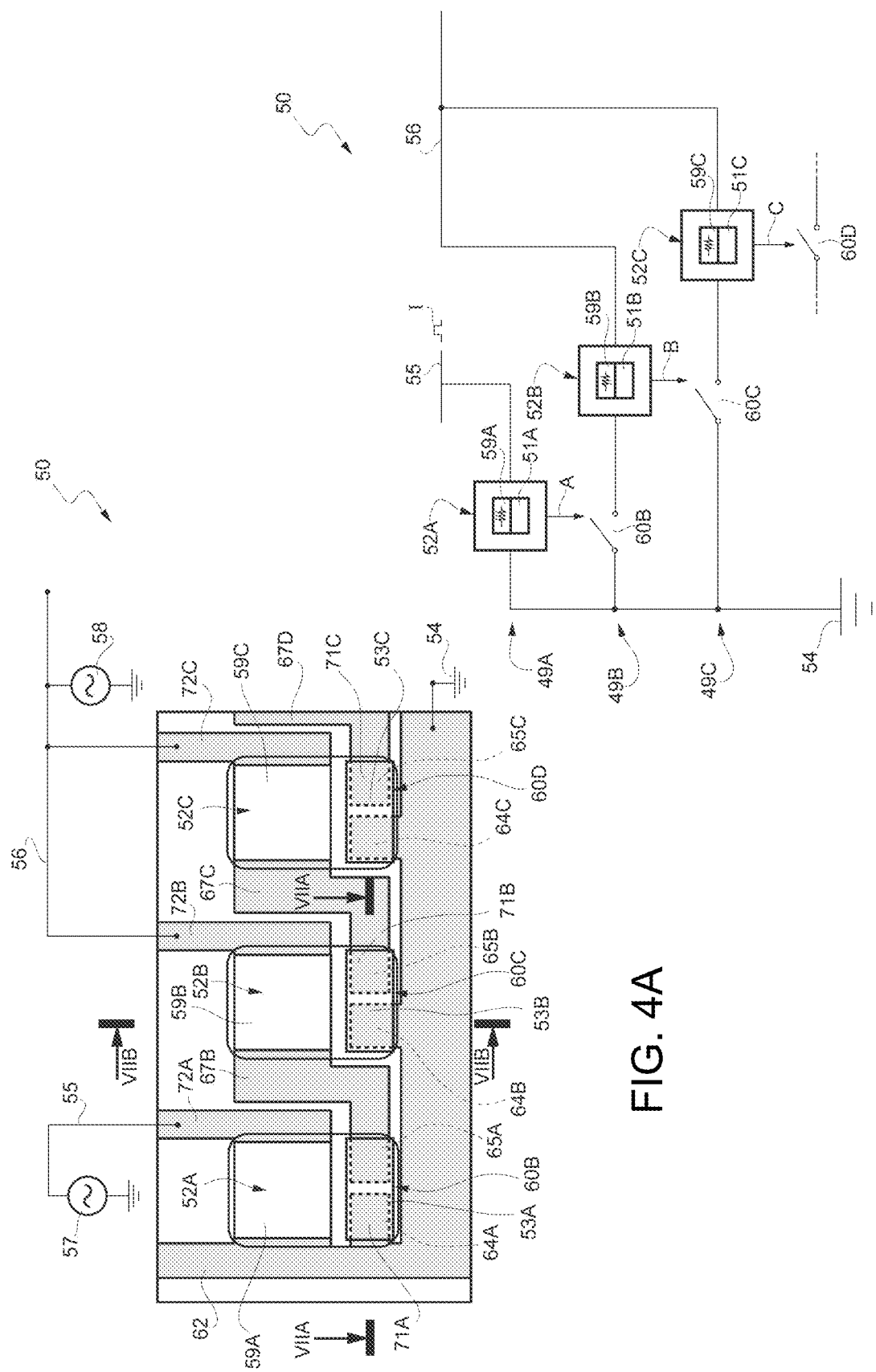
FIG. 4A is a simplified top view of the present microfluidic dispensing device, with parts removed for clarity.
FIG. 4B shows an equivalent scheme of the microfluidic dispensing device of FIG. 4A.

For understanding the principle underlying the present microfluidic dispensing device, reference be initially made to FIG. 4B which shows an equivalent electric circuit, thereafter also referred to as sequential activation circuit.

The microfluidic dispensing device 50 comprises a plurality of dispensing cells connected to each other so as to be activated sequentially. In the following figures, only three dispensing cells are shown, referred to as initial cell 49A, first sequential cell 49B and second sequential cell 49C, but it is to be understood that, in general, numerous other dispensing cells are arranged sequentially in succession to the second sequential cell 49C and activated sequentially, as discussed below.

In the following description, since the dispensing cells (except, in part, the initial cell 49A) have a similar structure, both the dispensing cells and the specific parts will be indicated with the generic number (for example 49 for the dispensing cells), not followed by a letter, when the description in general refers thereto, and with the number and the respective letter (A, B and C) when referring to a specific dispensing cell (here 49A, 49B, 49C) or parts thereof.

In the electrical diagram shown in FIG. 4B, the initial cell 49A is arranged between a ground line 54 and a first supply line 55 and comprises an initial dispensing chamber 52A, an initial heater 59A and an initial drop emission detection element 51A. An activation pulse I is provided to the first supply line 55 to activate the initial heater 59A, which is configured to cause a drop to be emitted (similarly to what is described with reference to FIG. 3); upon emitting a drop, the initial drop emission detection element 51A generates an initial activation signal A.

The sequential cells 49B, 49C have a structure similar to the initial cell 49A but also comprise a first, respectively a second switch, 60B, 60C, controlled by a preceding cell in the sequence (here the initial cell 49A and the first sequential cell 49B, respectively).

In detail, the first sequential cell 49B is arranged between the ground line 54 and a second supply line 56 and comprises a first sequential dispensing chamber 52B, a first sequential heater 59B, the first switch 60B and a first sequential drop emission detection element 51B. The first sequential heater 59B and the first switch 60B are arranged mutually in series between the ground line 54 and the second supply line 56. As indicated above, the first switch 60B is controlled by the initial drop emission detection element 51A and is configured, when receiving the initial activation signal A, to close the current path between the ground line 54 and the second supply line 56 and supply the first sequential heater 59B. The first sequential heater 59B is configured, when supplied, to cause a drop to be emitted into the first sequential dispensing chamber 52B; the first sequential drop emission detection element 51B is configured, upon detecting a drop, to generate a first activation signal B.

The second sequential cell 49C is arranged between the ground line 54 and the second supply line 56 and comprises a second sequential dispensing chamber 52C, a second sequential heater 59C, the second switch 60C and a second sequential drop emission detection element 51C. The second sequential heater 59C and the second switch 60C are arranged mutually in series between the ground line 54 and the second supply line 56. The second switch 60C is controlled by the first sequential drop emission detection element 51B and is configured, when receiving the first activation signal B, to close the current path between the ground line 54 and the second supply line 56 and supply the second sequential heater 59C. The second sequential heater 59C is configured, when supplied, to cause a drop to be emitted into the second sequential dispensing chamber 52C; the second sequential drop emission detection element 51C is configured, upon detecting a drop, to generate a second activation signal C to control a third switch 60D of a subsequent sequential cell, not shown in FIG. 4B. The heaters (59A-59C), acting as actuators for emitting a drop, the drop emission detection elements (51A-51C) and the switches (60B-60D), comprised in the sequential activation circuit shown in FIG. 4B, thus allow each cell 49A-49C, when activated for emitting a drop, to generate an activation signal of a subsequent cell in the sequence. Accordingly, a single initial signal (activation pulse I) allows all the sequential cells to be activated automatically and in sequence.

The sequential activation described above may be implemented in the manner shown in FIG. 4A.

FIG. 4A shows again three dispensing chambers (also identified here as initial chamber 52A, first chamber 52B and second chamber 52C). In general, however, as already indicated, the microfluidic dispensing device 50 comprises a large number of dispensing chambers, even a few thousand.

In the embodiment shown, the dispensing chambers 52A, 52B and 52C are arranged mutually adjacent, side by side along a line, and are fluidly connected to supply passages in a not-shown manner, for example formed as described above with reference to FIGS. 2A and 2B for passages 26.

In FIG. 4A, the first supply line 55 is coupled to a first voltage source 57, providing pulse-type voltage, and the second supply line 56 is coupled to a second voltage source 58, providing direct voltage. In the exemplary embodiment shown, the voltage sources 57, 58 are integrated in the microfluidic dispensing device 50 and provide, for example, pulse voltage of 15V and, respectively, direct voltage of 20 V. Alternatively to what shown, the voltage sources 57, 58 may be external to the microfluidic dispensing device 50, and coupled to the supply lines 55, 56 through contact pads not shown.

Figure 3:
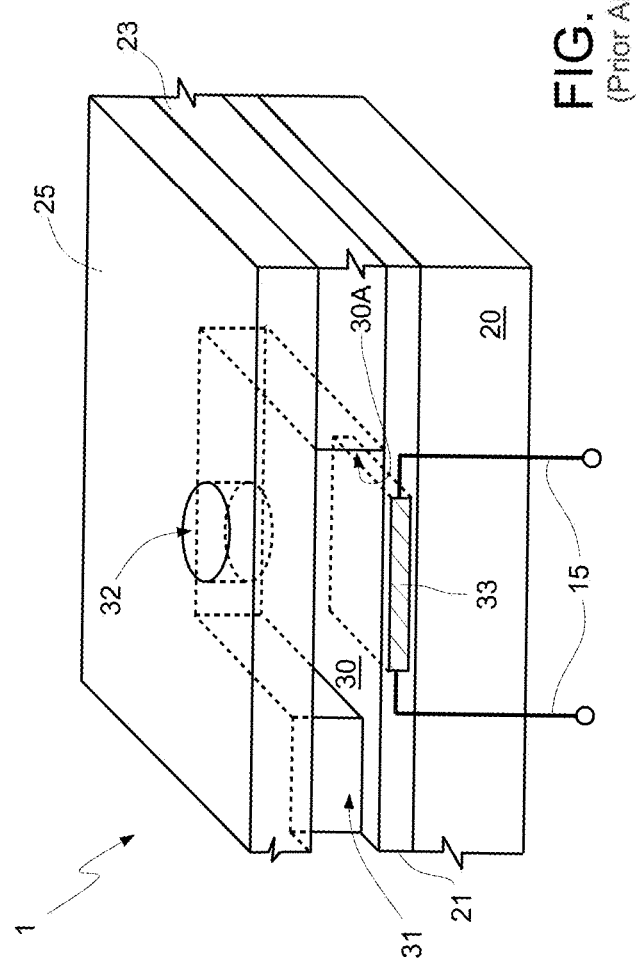
FIG. 3 is a section perspective view of a detail of FIG. 2A.

The dispensing chambers 52A-52C are equal to each other and may be formed, generally speaking, as shown in FIG. 3 and described in more detail below with reference to FIGS. 4 and 10A, 10B; in particular, each dispensing chamber 52A, 52B, 52C is formed by a compartment overlying a stack of layers forming the heaters 59A, 59B, 59C;

furthermore each dispensing chamber 52A-52C accommodates a first and a second conductive region 64A-64C and 65A-65C, contact regions 53A-53C and membranes 71A, 71B, 71C (forming the drop emission detection elements 51A-51C). The conductive regions 64A-64C and 65A-65C, together with the contact regions 53A-53C, form the switches 60B-60D and are electrically coupled to an initial connection track or line 72A, a first and a second sequential connection track 72B, 72C, a first, a second and a third track section 67B, 67C, 67D, which, together with the dispensing chambers 52A-52C and the heaters 59A-59C, form the sequential activation circuit of FIG. 4B.

In detail, the initial heater 59A associated with the initial chamber 52A is arranged between and is electrically coupled to a common ground track 62 (connected to the ground line 54) and the initial connection track 72A (connected to the first supply line 55). The common ground track 62 and the initial connection track 72A are formed in the same stack of layers forming the conductive regions 64A-64C and 65A-65C, the connection tracks 72A-72C and the track sections 67B, 67C, 67D.

The first conductive region 64A of the initial chamber 52A is connected to the common ground track 62 and the second conductive region 65A of the initial chamber 52A is connected and contiguous to the first track section 67B. The first conductive region 64A of the initial chamber 52A and the second conductive region 65A of the initial chamber 52A are arranged substantially in the initial chamber 52A, face each other and are electrically separated.

The initial membrane 71A also extends within the initial chamber 52A, adjacent to the initial heater 59A, and carries the initial contact region 53A on the bottom so that this region is vertically superimposed on and spaced, at rest, from the first and the second conductive regions 64A, 65A of the initial chamber 52A. The initial membrane 71A is configured to deform when a drop is emitted (as described in detail hereinbelow).

The initial membrane 71A thus forms the initial drop detection element 51A; the initial contact region 53A, together with the first conductive region 64A of the initial chamber 52A and the second conductive region 65A of the initial chamber 52A, forms the first switch 60B of FIG. 4B.

The first sequential heater 59B associated with the first sequential chamber 52B is arranged between the second conductive region 65A of the initial chamber 52A (through the first track section 67B) and the first sequential connection track 72B (connected to the second supply line 56); furthermore the first sequential heater 59B is electrically coupled thereto.

Accordingly, the first sequential heater 59B may be electrically coupled to the common ground line 62 through the first switch 60B of FIG. 4B.

The first conductive region 64B of the first sequential chamber 52B is connected to the common ground track 62 and the second conductive region 65B of the first sequential chamber 52B is connected to the second track section 67C. The first conductive region 64B of the first sequential chamber 52B and the second conductive region 65B of the first sequential chamber 52B are arranged substantially in the first sequential chamber 52B, face each other and are electrically separated.

The first sequential membrane 71B also extends within the first sequential chamber 52B, adjacent to the first sequential heater 59B and carries the first sequential contact region 53B on the bottom so that this region is vertically superimposed on and spaced, at rest, from the first and the second conductive regions 64B, 65B of the first sequential chamber 52B. The first sequential membrane 71B is configured to deform when a drop is emitted (as described in detail hereinbelow).

The first sequential membrane 71B thus forms the first sequential drop detection element 51B; the first sequential contact region 53B, together with the first conductive region 64B of the first sequential chamber 52B and the second conductive region 65B of the first sequential chamber 52B, forms the second switch 60C of FIG. 4B.

The second sequential heater 59C associated with the second sequential chamber 52C is arranged between the second conductive region 65B of the first sequential chamber 52B (through the second track section 67C) and the second sequential connection track 72C (connected to the second supply line 56); furthermore the second sequential heater 59C is electrically coupled thereto.

Accordingly, the second sequential heater 59C may be electrically coupled to the common ground line 62 through the second switch 60C of FIG. 4B.

The first conductive region 64C of the second sequential chamber 52C is connected to the common ground track 62 and the second conductive region 65C of the second sequential chamber 52C is connected to the third track section 67D. The first conductive region 64C of the second sequential chamber 52C and the second conductive region 65C of the second sequential chamber 52C are arranged substantially in the second sequential chamber 52C, face each other and are electrically separated from each other.

The second sequential membrane 71C also extends within the second sequential chamber 52C, adjacent to the second sequential heater 59C and carries the second sequential contact 53C on the bottom region so that this region is vertically superimposed on and spaced, at rest, from the first and the second conductive regions 64C, 65C of the second sequential chamber 52C. The second sequential membrane 71C is configured to deform when a drop is emitted (as described in detail below).

The second sequential membrane 71C thus forms the second sequential drop detection element 51C; the second sequential contact region 53B, together with the first conductive region 64C of the second sequential chamber 52C and the second conductive region 65C of the second sequential chamber 52C, forms the third switch 60D for sequentially supplying a subsequent heater in the sequence, not shown here.

In use, when it is desired to activate the microfluidic dispensing device 50, the first voltage source 57 generates the activation signal I. Accordingly, the initial heater 59A is crossed by a pulse current, heats up and causes a drop to be emitted by the initial chamber 52A, similarly to what described in Italian patent application No. 102018000005372, mentioned above. The pressure variation associated with the emission of the drop by the initial chamber 52A causes the deformation of the initial membrane 71A, which bends towards the first and the second conductive regions 64A, 65A of the initial chamber (in a direction perpendicular to the plane of FIG. 4A), causing a similar deflection of the initial contact region 53A which comes into physical and electrical contact with both the first conductive region 64A and the second conductive region 65A of the initial chamber 52A, connecting them and closing the first switch 60B.

Noteworthy, the first switch 60B remains closed only as long as the initial membrane 71A is deformed; after the drop has been emitted, the pressure in the initial chamber 52A decreases and the initial membrane 71A returns to its rest position, by reopening the first switch 60B.

Closing the first switch 60B determines the electrical connection of the first sequential heater 59B to the common ground track 62 through the first track section 67B. As a result, the first sequential heater 59B heats up and causes a drop to be emitted by the first sequential chamber 52B.

In turn, the pressure variation associated with the emission of the drop by the first sequential chamber 52B causes the deformation of the first sequential membrane 71B and the first sequential contact region 53B, which comes into physical and electrical contact with both the first conductive region 64B and the second conductive region 65B of the first sequential chamber 52B, connecting them and closing the second switch 60C.

As a result a drop is emitted by the second sequential chamber 52C and the second sequential membrane 71C is deformed, similarly to what described above for the initial membrane 71A and the first sequential membrane 71B.

In this manner, the sequential emission of drops by all the dispensing chambers (not shown) in the microfluidic dispensing device 50 may be obtained.

In the microfluidic dispensing device 50 of FIGS. 4 and 4A, as indicated, all the dispensing chambers 52 are arranged sequentially and are activated in succession.

Figure 5:
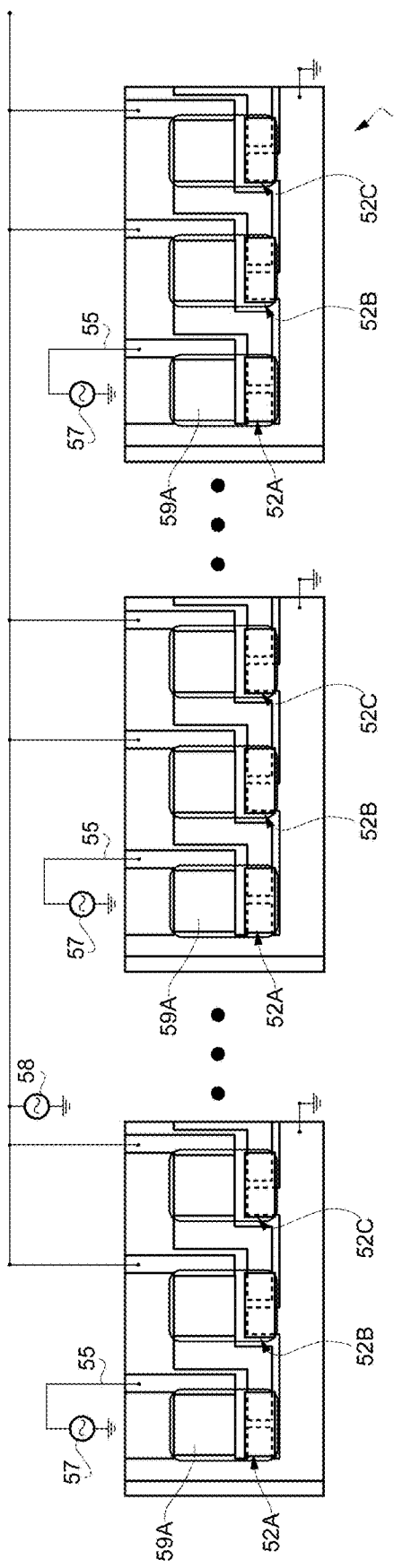
FIGS. 5 and 6 show different embodiments of the present microfluidic dispensing device, in simplified top views.
Figure 6:
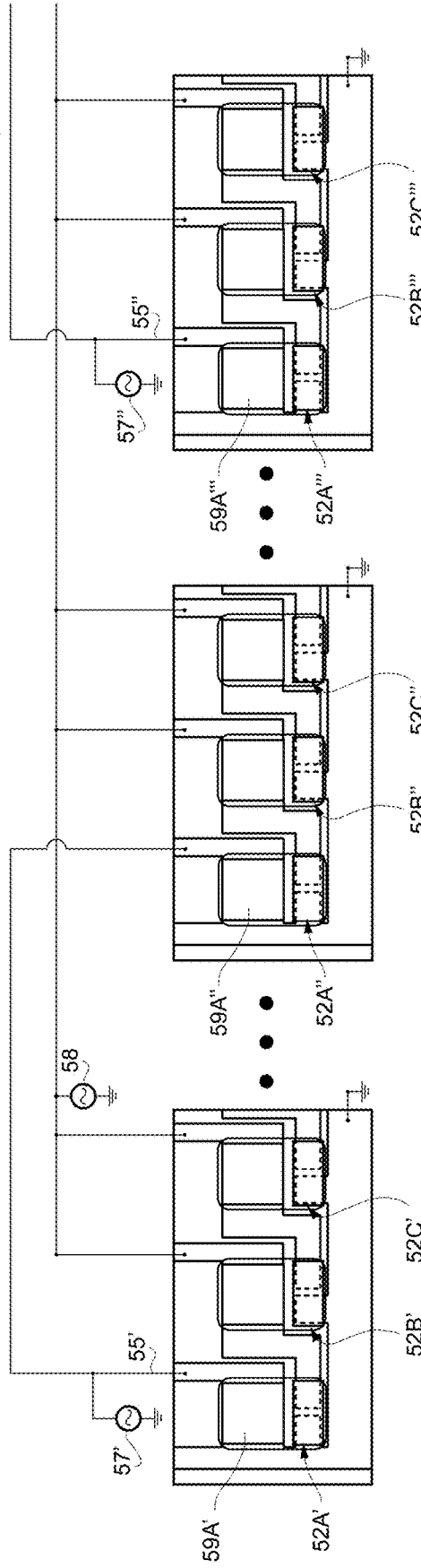

Alternatively, the dispensing chambers 52 may be grouped, so that groups of dispensing cells or dispensing modules are controlled simultaneously, as for example shown in FIG. 5 or 6.

In detail, FIG. 5 shows a dispensing device 100 having a plurality of dispensing modules (three in FIG. 5). Each dispensing module comprises a plurality of dispensing chambers 52 formed and arranged in the manner shown in FIG. 4A; accordingly, the elements common to FIG. 4A have been provided with the same reference numbers and will not be further described.

In particular, each dispensing module comprises an initial chamber 52A and a plurality of sequential chambers (in FIG. 5, a first and a second sequential chamber 52B, 52C; however, as for the device 50 of FIG. 4A, generally each dispensing module may comprise a large number of dispensing chambers 42, for example even a few hundred or a few thousand).

In FIG. 5, each initial heater 59A is connected to a respective first voltage source 57, and all the other heaters (first and second sequential heaters 59B, 59C of all the dispensing modules) are connected to the second voltage source 58.

In this manner, for each dispensing module, the respective initial heater 59A controls the subsequent sequential heaters of the same module, substantially reducing the number of connection wires necessary to control the dispending device 100.

Figure 1:
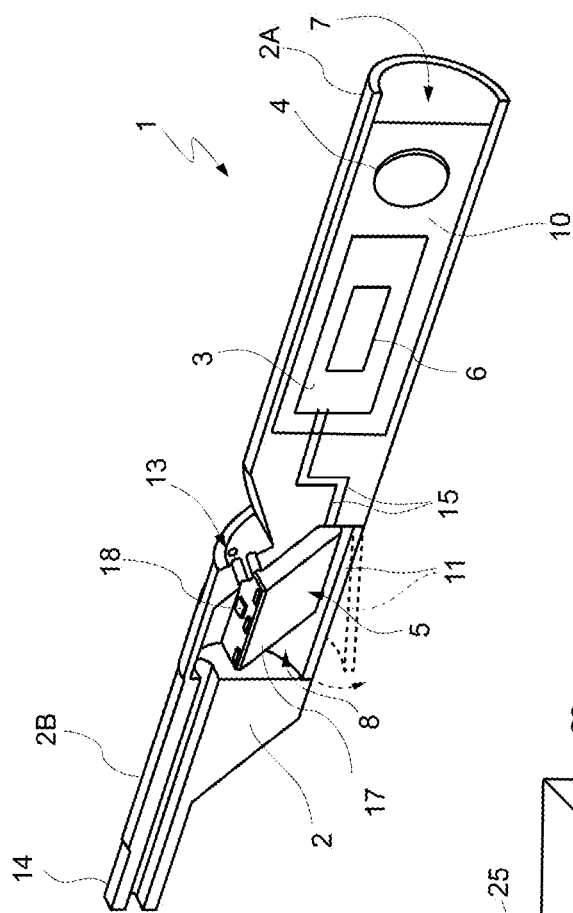
FIG. 1 is a longitudinal-section perspective view of a known electronic cigarette.

Furthermore, the activation of each dispensing module may take place independently: for example, the dispensing chambers 52 of each dispensing module may be supplied by different liquids contained in different parts of the tank (not shown, similar to tank 17 of FIG. 1) and be activated simultaneously, so as to obtain the simultaneous release and mixing of drops of liquid of different type.

Alternatively, the dispensing modules may be activated selectively; for example, in some operating modes, all the dispensing modules are operated; in other operating modes, only some dispensing modules are operated, for example a half or a third. In this manner, dispensing of different selectable quantities of drops may be obtained. Or the dispensing modules may be activated at different times, as may be desired depending on design considerations.

FIG. 6 shows a dispensing device 150, three dispensing modules whereof are shown.

Here again, each dispensing module is formed as the group of dispensing chambers 52 shown in FIG. 4A; in detail, the first dispensing module is formed by a plurality of dispensing chambers 52A', 52B', 52C', with heaters 59A', 59B', 59C' and a set of drop emission detection elements 51A', 51B', 51C' associated therewith. The second dispensing module is formed by a plurality of dispensing chambers 52A", 52B", 52C", with heaters 59A", 59B", 59C" and a set of drop emission detection elements 51A", 51B", 51C" associated therewith. The third dispensing module is formed by a plurality of dispensing chambers 52A'", 52B'" ", 52C'", with heaters 59A'", 59B'", 59C'" and a set of drop emission detection elements 51A'",51B'",51C'" associated therewith.

In this embodiment, pairs of initial heaters 59A are connected to a same first voltage source. In particular, FIG. 6 shows two initial heaters 59A', 59A" connected to a same first voltage source, indicated here with 57', through a first pulse supply line 55', and a further initial heater 59A'" (together with a subsequent initial heater not shown) is connected to another first voltage source, indicated here with 57", through a second pulse supply line 55".

Here again, all the other heaters (first and second sequential heaters 59B', 59C', 59B", 59C") are connected to the second voltage source 58.

This solution also allows modules for dispensing fractional quantities of drops or dispensing according to predetermined time sequences to be selectively activated.

The manufacturing process of the microfluidic dispensing device 50 of FIG. 4A is shown in FIGS. 7A, 8A, 9A, 10A, as regards the area of the first and second switches 60B, 60C and in FIGS. 7B, 8B, 9B and 10B as regards the area of the first sequential chamber 52B. The structures relating to the subsequent switches, the initial chamber 52A, the second sequential chamber 52C and the other cells of the sequence (not shown) are formed simultaneously, as apparent to the skilled in the art. The dispensing devices 100 and 150 of FIGS. 5 and 6 have the same structure and what described herein below also applies thereto.

In detail, FIGS. 7A and 7B show an intermediate structure 80 relating to the manufacture of the microfluidic dispensing device 50 after the first initial steps.

In particular, the intermediate structure 80 of FIG. 7A comprises a substrate 200 of semiconductor material, for example silicon, overlaid by a first insulating layer 201, for example of silicon oxide. FIG. 7A also shows metal regions obtained by depositing and shaping a metal layer 202 (for example of copper-doped aluminum-AlCu) on the first insulating layer 201 and including a first metal region 202A (forming the common ground track 62 and the first conductive region 64A of the initial chamber 52A, contiguous to each other and in electrical continuity), a second metal region 202B (forming the second conductive region 65A of the initial chamber 52A and the first track section 67B), a third metal region 202C (forming the first conductive region 64B of the first sequential chamber 52B), and a fourth metal region 202D (forming the second conductive region 65B of the first sequential chamber 52B and the second track section 67C). FIG. 7B shows part of the third metal region 202C, forming here part of the first conductive region 64B of the first sequential chamber 52B. In this step, in a not-shown manner, the connection tracks 72A-72C are also formed.

Furthermore, the intermediate structure 80 comprises portions of a sacrificial layer 203, for example of silicon oxide, deposited above the metal layer 202 (or, where the latter has been removed, above the first insulating layer 201) and defined so as to form (FIG. 7A) a first insulating region 203A, partially covering the first metal region 202A; a first sacrificial region 203B (where it is desired to form the first switch 60B, FIG. 4A), between and partially covering the first metal region 202A and the second metal region 202B; a second sacrificial region 203C (where it is desired to form the second switch 60C, FIG. 4A), above and laterally surrounding the second metal region 202B and arranged between the latter and the fourth metal region 202D. Furthermore, the sacrificial layer 203 forms (FIG. 7B) a second insulating region 203D, where it is desired to form the first sequential heater 59B; in FIG. 7B the second sacrificial region 203C is also visible.

A resistive layer 204 of material suitable for forming the heaters 59A-59C, for example of polycrystalline silicon, Al, Pt, TiN, TiAlN, TaSIN, TiW, has already been deposited above the sacrificial layer 203 and defined. In FIG. 7B, the resistive layer 204 forms a heater region 204A, forming the first sequential heater 59B; furthermore, it may form a first protective region 204B, covering the second insulating region 203A (FIG. 7A).

A connection layer 205, for example of metal, such as aluminum, has already been deposited above the resistive layer 204 and defined, so as to form (FIG. 7A) a first and a second connection region 205A, 205B, overlying, respectively, the first sacrificial region 203B and the second sacrificial region 203C and forming the contact regions 53A, 53B of FIG. 4A. The second connection region 205B is also visible in FIG. 7B.

A first protection layer 206 of dielectric material, for example of SiN, which in FIGS. 7A and 7B is continuous and which, in general, is opened where it is desired to form the contacts with the metal layer 202, has already been deposited above the connection layer 205, and defined.

Above the first protection layer 206, a heat distribution layer 207, formed, for example, by a layer of Tantalum (Ta) underlying a succession of layers such as silicon oxynitride (SiON) and tetraethyl orthosilicate (TEOS) with anti-reflective functionality, has already been deposited and defined, so as to form a heat distribution region 207A (FIG. 7B), at the first sequential heater 59B.

Furthermore, above the previous layers, a second protection layer 208, for example of polymeric material, such as TMMR produced by Tok, Tokyo Ohka Kogyo Co. Inc., which is removed here only above the heat distribution region 207A (FIG. 7B), has already been deposited and defined.

Figure 8A:
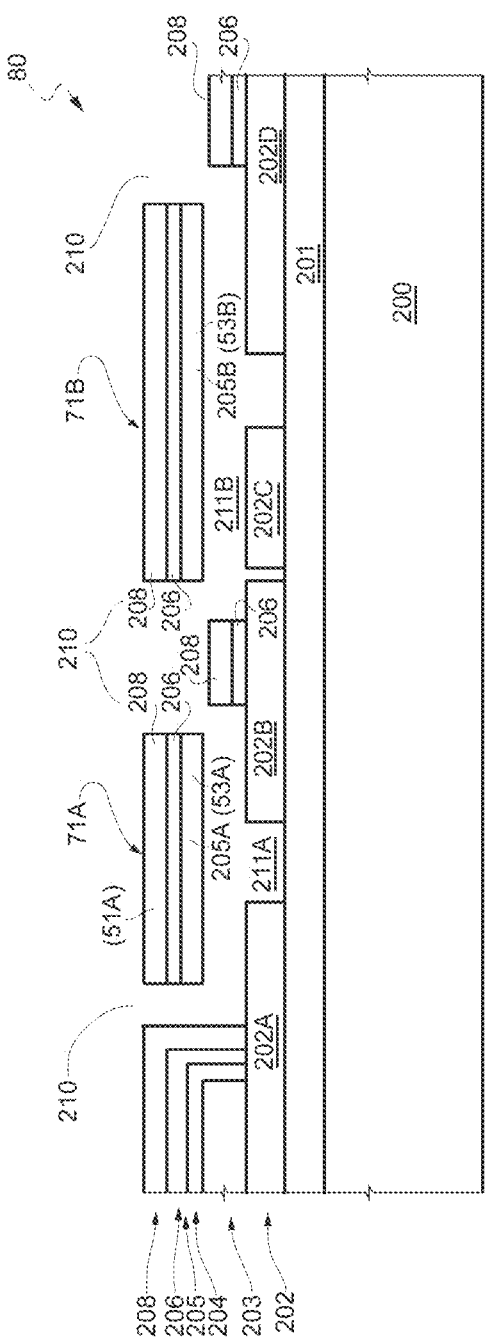

Thereafter, FIGS. 8A and 8B, the first protection layer 206 and the second protection layer 208 are selectively removed to form membrane openings 210 and reach the first sacrificial region 203B and the second sacrificial region 203C (FIG. 7A) which are then removed through a special etching (for example with hydrofluoric acid) to form a first and a second cavity 211A, 211B (FIG. 8A) below the first and second contact regions 205A, 205B. The second cavity 211B is also visible in FIG. 8B. Accordingly, the portions of the protection layers 206, 208 above the cavities 211A, 211B form the initial membrane 71A and the first sequential membrane 71B; the first and second contact regions 205A, 205B, forming the contact regions 53A and 53B, respectively, are suspended above the first and second metal regions 202A, 202B and the third and fourth metal regions 202C, 202D, respectively, forming the switches 60B, 60C.

Figure 8B:
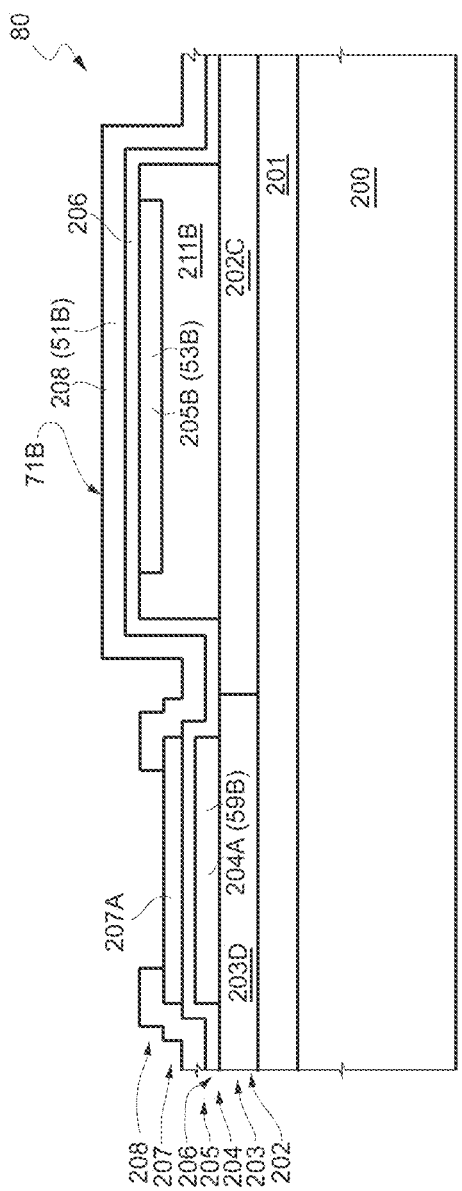

In practice, in the embodiment shown, the initial membrane 71A and the first sequential membrane 71B, as well as the second sequential membrane 71C, are contiguous to the respective heaters 59A-59C (of which in FIG. 8B only the first sequential heater 59B formed by the heater region 204A is visible).

Figure 9A:
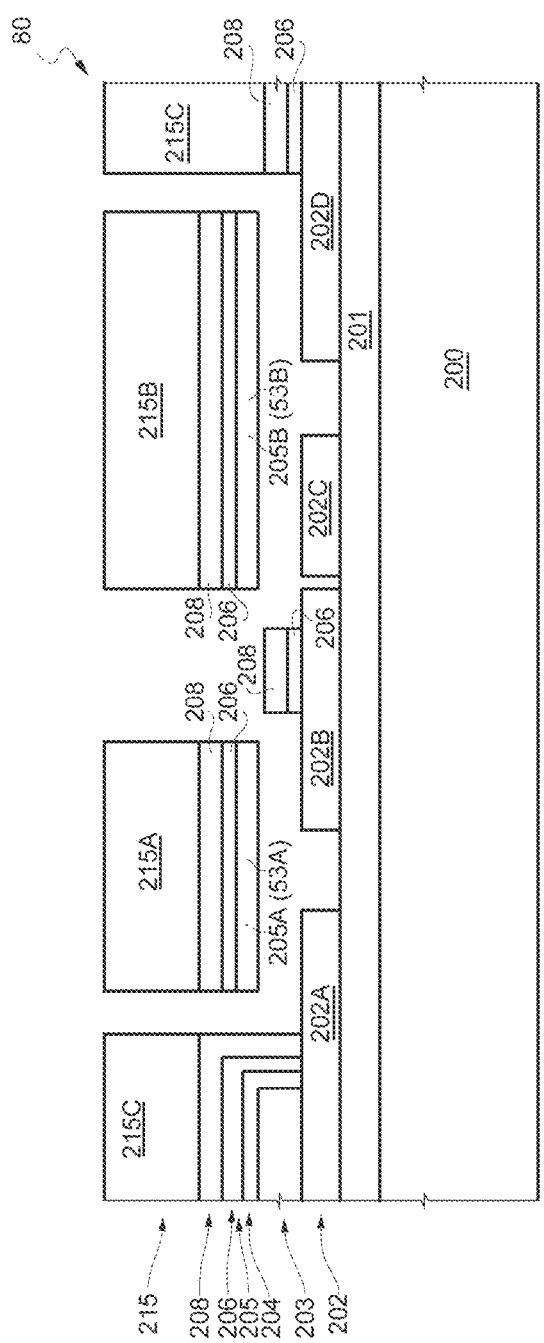
Figure 9B:
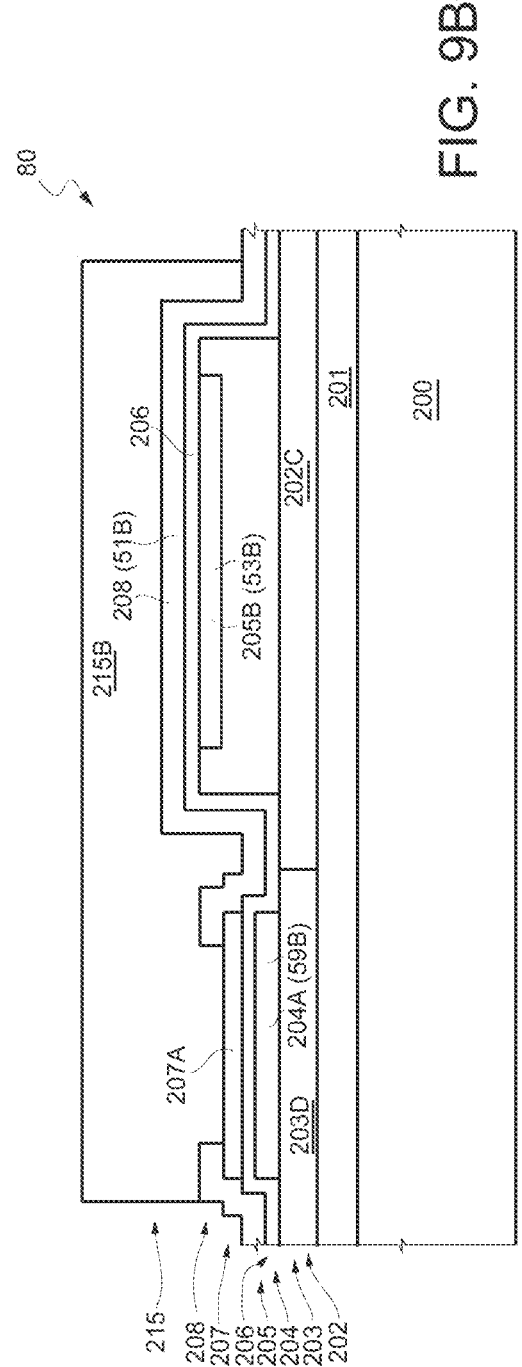

Thereafter, FIGS. 9A and 9B, the intermediate structure 80 is covered by a shaping layer 215, for example of photoresist, which is shaped so as to form a first and a second chamber sacrificial region 215A, 215B (at areas of the device 50 where it is desired to form the initial chamber 52A and the first sequential chamber 52B) as well as lightening regions 215C (at portions of the microfluidic dispensing device 50 where it is desired to form lightening cavities).

Then, FIGS. 10A and 10B, a structural layer 216, for example of TMMF produced by Tok, Tokyo Ohka Kogyo Co. Inc., is deposited and defined so that the structural layer 216 has a chamber opening 217 (FIG. 10B) above the area of the intermediate structure 80 where it is desired to form the first sequential chamber 52B (as well as, in a non-visible manner, the other dispensing chambers 52. Thereafter, the first and second chamber sacrificial regions 215A, 215B are completely removed through the chamber opening 217, forming the initial chamber 52A and the first sequential chamber 52B. The chamber opening 217 also forms a nozzle for the first sequential chamber 52B. In practice, the structural layer 216 here forms both lateral delimitation walls of the dispensing chambers and a nozzle plate.

Final steps, not shown, follow for thinning the intermediate structure 80 and forming rear channels, in a per se known manner, for the fluidic connection of the dispensing chambers to one or more tanks (not shown), obtaining the microfluidic dispensing device 50 of FIG. 4A.

The microfluidic dispensing device 50, 100, 150 described herein has numerous advantages.

In particular, the sequential activation of the cells 49 allow the activation signals which, in one embodiment, may be limited to a single signal for all the cells, to be considerably reduced, obtaining a semi-automatic behavior of the dispensing device. As a result the present microfluidic dispensing device requires little integration area of the contact areas, has small overall dimensions and low cost, therefore it may also be used in small and/or cheap portable apparatus.

Furthermore, it is no longer necessary to have a control unit, such as an ASIC, for the activation, reducing system costs, both when the control unit is outside and when it is within the dispensing device.

The described microfluidic dispensing device also allows current consumption to be reduced, as the semi-automatic activation mechanism described allows the number of active components, for example transistors, necessary for the operation of the dispensing device, to be reduced.

The specific implementation shown in FIGS. 7A-10B allows the switches 60B, 60C, 60D to be formed using the same layers used to form other structures, such as the heaters 59, with simple modifications of masks and possibly adding the steps for forming the membrane openings 210 and removing sacrificial regions, with manufacturing costs comparable to those of the known devices.

Finally, it is clear that modifications and variations may be made to the microfluidic dispensing device, the manufacturing process and the dispensing method described and illustrated herein without thereby departing from the scope of the present disclosure, as defined in the attached claims.

For example, although the present description refers to a device thermally actuated by heaters, the same solution may also apply to actuations of a different type, for example of a piezoelectric type, wherein a piezoelectric actuator causes the deformation of an actuation membrane for emitting the drop. In this case, part of the actuation membrane might be used to close the switch associated.

Furthermore, the spatial arrangement of the dispensing chambers may be any, depending on the application. In particular, they may be arranged side by side on a line, straight or curved, or on a closed line, such as a circumference (for example as in the solution shown in FIGS. 2A and 2B), be arranged on one or more lines, for example on multiple concentric circumferences (as also shown in FIGS. 2A and 2B).

The shape and specific implementation of the dispensing chambers may vary with respect to what shown; in particular, the dispensing chambers may have any geometric shape, different from the rectangular one shown. Furthermore, the implementation shown in FIGS. 7A-10B may vary; for example, instead of having an integrated layer forming both the walls delimiting the dispensing chambers and the nozzle plate, a separate nozzle plate may be formed, bonded to the structure forming the dispensing chambers.

The shape, size, number and position of the nozzles in each dispensing chamber may differ, depending on the application.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A microfluidic dispensing device, comprising:
 a plurality of chambers, each chamber having an inlet configured to receive a liquid to be dispensed and a nozzle configured to emit a drop of liquid, the plurality of chambers forming a sequence of chambers;
 a plurality of actuators, each actuator being associated with a respective chamber and configured to receive a respective actuation quantity and cause a drop of liquid to be emitted by the nozzle of the respective chamber;
 a plurality of drop emission detection elements, one for each chamber, each drop emission detection element being configured to generate an actuation command upon detecting the emission of a drop of liquid from the nozzle of a respective chamber; and a sequential activation electric circuit including a plurality of sequential activation elements, one for each chamber, each sequential activation element being coupled to the drop emission detection element associated with the respective chamber and to an actuator associated with a chamber following the respective chamber in the sequence of chambers, each sequential activation element being configured to receive the actuation command from the drop emission detection element associated with the respective chamber and activate the actuator associated with the subsequent chamber in the sequence of chambers.

2. The device according to claim 1, wherein each sequential activation element comprises a switch controlled by the respective drop emission detection element, the sequential activation electric circuit further including a first supply line, each switch being arranged between the first supply line and the actuator associated with the subsequent chamber in the sequence of chambers, each switch being further configured to electrically couple the first supply line to the actuator associated with the subsequent chamber in the sequence of chambers.

3. The device according to claim 2, further comprising:
a second supply line; and
a plurality of conductive lines, one for each chamber, each conductive line being coupled between the second supply line and the actuator associated with the respective chamber.

4. The device according to claim 3, further comprising:
a first pulse supply line; and
an initial chamber having an initial inlet, an initial nozzle and an initial actuator, the initial actuator being coupled between the first supply line and the first pulse supply line.

5. The device according to claim 4, wherein the initial chamber, the plurality of chambers, the plurality of drop emission detection elements and the sequential activation electric circuit form a first dispensing module, the device further including:
a second dispensing module including:
a second initial chamber;
a second plurality of chambers;
a second plurality of drop emission detection elements; and
a second sequential activation electric circuit,
wherein each chamber of the second plurality of chambers of the second dispensing module includes a second switch and a second actuator, each second actuator being coupled to the second supply line and being couplable to the first supply line through the respective second switch, and
wherein the second initial chamber of the second dispensing module includes a second initial actuator coupled between the first supply line and a further pulse supply line.

6. The device according to claim 5, wherein the pulse supply line coupled to the initial actuator of the first dispensing module and the further pulse supply line are mutually coupled.

7. The device according to claim 6, further comprising:
a third dispensing module including:
a third initial chamber;
a third plurality of chambers;
a third plurality of drop emission detection elements; and
a third sequential activation electric circuit,
wherein each chamber of the third plurality of chambers of the third dispensing module includes a third switch and a third actuator, each third actuator being coupled to the second supply line and being couplable to the first supply line through the respective third switch, and
wherein the initial chamber of the third dispensing module includes a third initial actuator coupled between the first reference potential line and a third pulse supply line.

8. The device according to claim 5, wherein the first pulse supply line and the further pulse supply line are mutually decoupled.

9. The device according to claim 1, wherein each chamber includes:
a first and a second conductive region, the first and the second conductive regions being adjacent and mutually insulated from one another, the first conductive region coupled to the first supply line, and the second conductive region coupled to the actuator associated with the subsequent chamber in the sequence of chambers; and
a suspended membrane configured to deform when a respective nozzle emits a drop and remotely overlying, at rest, the first and the second conductive region, the suspended membrane forming the drop emission detection element and being integral with a contact region of conductive material, the contact region forming, together with the first and the second conductive regions, the sequential activation element of the respective chamber and being shaped to electrically couple the first and the second conductive regions in a deformed condition of the suspended membrane.

10. The device according to claim 9, comprising:
a substrate;
a plurality of electrical connection regions extending on the substrate, the plurality of electrical connection regions including the first and the second conductive regions of each chamber; and
a plurality of heaters, one for each chamber, each heater being superimposed on the substrate and adjacent to the respective suspended membrane of each chamber,
wherein, in each chamber, the contact region extends above and faces the respective first and second conductive regions,
wherein, at rest, a gap extends between each contact region and the respective first and second conductive regions, and
wherein the suspended membrane extends above a respective contact region.

11. The device according to claim 10, wherein the suspended membrane includes a polymeric material region.

12. The device according to claim 11, further comprising a dielectric layer covering the plurality of heaters and arranged between the polymeric material regions and the respective contact regions.

13. The device according to claim 1, wherein each actuator is arranged within a respective chamber and each drop emission detection element is arranged in proximity to or within a respective chamber.

14. The device according to claim 1, wherein the actuators are resistive heaters.

15. A microfluidic dispensing device, comprising:
a sequence of chambers each having an inlet and a nozzle configured to emit a drop of liquid;
a plurality of actuators each associated with a respective chamber and configured to cause a drop of liquid to be emitted by the nozzle of the respective chamber;

a plurality of drop emission detection elements each coupled to a respective chamber;

a sequential activation electric circuit including a plurality of sequential activation elements each coupled to a respective drop emission detection element and a respective actuator downstream from the drop emission detection element and configured to receive an actuation command from the drop emission detection element and to activate the corresponding actuator.

16. The device according to claim 15, wherein each sequential activation element includes a switch controlled by the respective drop emission detection element.

17. The device according to claim 16, wherein the sequential activation electric circuit further includes a first supply line, each switch being arranged between the first supply line and the actuator associated with the subsequent chamber in the sequence of chambers, each switch being further configured to electrically couple the first supply line to the actuator associated with the subsequent chamber in the sequence of chambers.

18. The device according to claim 17, further comprising:
a second supply line; and
a plurality of conductive lines, one for each chamber, each conductive line being coupled between the second supply line and the actuator associated with the respective chamber.

19. A microfluidic dispensing device, the microfluidic dispensing device comprising:
a first chamber and a second chamber;
a first actuator coupled to the first chamber and configured to cause the first chamber to emit a first drop of liquid;
a first drop emission detection element configured to detect that the first chamber has output the first drop of liquid;
a first activation element coupled to the first drop emission detection element;
a second actuator coupled to the second chamber and configured to receive an indication from the first activation element that the first drop have been emitted from the first chamber and to cause the second chamber to emit a second drop of liquid responsive to the first chamber emitting the first drop of liquid;
a second drop emission detection element configured to detect that the second chamber has output the second drop of liquid; and
a second activation element coupled to the second drop emission detection element.

20. The microfluidic dispensing device of claim 19, comprising:
a third chamber; and
a third actuator coupled to the second activation element and the third chamber.

* * * * *